(12) United States Patent
Reaney

(10) Patent No.: US 6,414,171 B1
(45) Date of Patent: Jul. 2, 2002

(54) METHOD FOR COMMERCIAL PREPARATION OF CONJUGATED LINOLEIC ACID FROM BY-PRODUCTS OF VEGETABLE OIL REFINING

(75) Inventor: Martin J. T. Reaney, Saskatoon (CA)

(73) Assignee: Her Majesty in Right of Canada, as represented by the Minister of Agriculture & Agri-Food Canada, Ottawa (CA)

( * ) Notice: Subject to any disclaimer, the term of this patent is extended or adjusted under 35 U.S.C. 154(b) by 0 days.

(21) Appl. No.: 09/994,060

(22) Filed: Nov. 27, 2001

(51) Int. Cl.⁷ ............................................. C07B 35/08
(52) U.S. Cl. ..................................................... 554/126
(58) Field of Search ......................................... 584/126

(56) References Cited

U.S. PATENT DOCUMENTS

| | | |
|---|---|---|
| 2,242,230 A | 5/1941 | Burr |
| 2,343,644 A | 3/1944 | Cawley |
| 2,350,583 A | 6/1944 | Bradley |
| 2,389,260 A | 11/1945 | Kirschenbauer |
| 4,164,505 A | 8/1979 | Krajca |
| 4,376,711 A | 3/1983 | Shaub |
| 4,381,264 A | 4/1983 | Struve |
| 4,393,043 A | 7/1983 | Koulbanis |
| 5,053,534 A | 10/1991 | Cosgrove |
| 5,070,104 A | 12/1991 | Pariza |
| 5,194,640 A | 3/1993 | Cosgrove |
| 5,428,072 A | 6/1995 | Cook |
| 5,430,066 A | 7/1995 | Cook |
| 5,504,114 A | 4/1996 | Cook |
| 5,554,646 A | 9/1996 | Cook |
| 5,585,400 A | 12/1996 | Cook |
| 5,674,901 A | 10/1997 | Cook |
| 5,760,083 A | 6/1998 | Cook |
| 5,770,217 A | 6/1998 | Kutilek |
| 5,892,074 A | 4/1999 | Seidel |
| 5,986,116 A | * 11/1999 | Iwata et al. .................. 554/126 |

OTHER PUBLICATIONS

Soap in Oil Titrimetric Method, AOCS Recommended Practice Cc 17–95.
Free Fatty Acids, AOCCS Official Method Ca 5a–40.
Drying Oils and Resins, Industrial and Engineering Chemistry, pp237–242, Feb. 1942.

* cited by examiner

Primary Examiner—Deborah D. Carr
(74) Attorney, Agent, or Firm—Dowell & Dowell, P.C.

(57) ABSTRACT

Methods for quantitative conversion of soapstock, lecithin gums, deodorizer distillate and other by-products of vegetable oil refining containing interrupted double bond systems, to products with conjugated double bonds, using a reduced amount of alkali. Less than one mole of alkali per mole of acyl group present is required, thereby greatly reducing the need for added caustic compared with methods using oils, fatty acids and esters as starting materials. The preferred starting materials are soapstocks derived from vegetable oils rich in linoleic acid.

12 Claims, No Drawings

METHOD FOR COMMERCIAL PREPARATION OF CONJUGATED LINOLEIC ACID FROM BY-PRODUCTS OF VEGETABLE OIL REFINING

FIELD OF THE INVENTION

This invention relates to a process for the preparation of conjugated linoleic acid (CLA). The process overcomes the high input costs of alkali and oil by using soapstock, soap and other vegetable oil refining by-products as the source of linoleate moieties. Surprisingly, refining wastes enriched in soaps may be converted to CLA with the addition of substoichiometric amounts of alkali. The reaction is unique in that it allows the utilization of an inexpensive by-product of vegetable oil refining to produce CLA.

BACKGROUND OF THE INVENTION

Conjugated linoleic acid is the trivial name given to a series of eighteen carbon diene fatty acids with conjugated double bonds. Applications of conjugated linoleic acids vary from treatment of medical conditions such as anorexia (U.S. Pat. No. 5,430,066) and low immunity (U.S. Pat. No. 5,674,901) to applications in the field of dietetics where CLA has been reported to reduce body fat (U.S. Pat. No. 5,554,646) and to inclusion in cosmetic formulae (U.S. Pat. No. 4,393,043).

CLA shows similar activity in veterinary applications. In addition, CLA has proven effective in reducing valgus and varus deformity in poultry (U.S. Pat. No. 5,760,083), and attenuating allergic responses (U.S. Pat. No. 5,585,400). CLA has also been reported to increase feed conversion efficiency in animals (U.S. Pat. No. 5,428,072). CLA-containing bait can reduce the fertility of scavenger bird species such as crows and magpies (U.S. Pat. No. 5,504,114).

Industrial applications for CLA also exist where it is used as a lubricant constituent (U.S. Pat. No. 4,376,711). CLA synthesis can be used as a means to chemically modify linoleic acid so that it is readily reactive to Diels-Alder reagents (U.S. Pat. No. 5,053,534). In one method linoleic acid was removed from oleic acid by first conjugation then reaction with maleic anhydride followed by distillation (U.S. Pat. No. 5,194,640).

Conjugated linoleic acid occurs naturally in ruminant depot fats. The predominant form of CLA in ruminant fat is the cis,trans-9,11-octadecadienoic acid which is synthesized from linoleic acid in the rumen by micro-organisms like *Butryvibrio fibrisolvens*. The level of CLA found in ruminant fat is in part a function of dietary cis,cis-9,12-octadecadienoic acid and increase marginally in ruminant milk and depot fat by feeding linoleic acid (U.S. Pat. No. 5,770,247).

CLA may also be prepared by any of several analytical and preparative methods. Pariza and Ha pasteurized a mixture of butter oil and whey protein at 85° C. for 5 minutes and noted elevated levels of CLA in the oil (U.S. Pat. No. 5,070,104). CLA produced by this mechanism is predominantly a mixture of cis,trans-9,11-octadecadienoic acid and trans,cis-10,12-octadecadienoic acid.

CLA has also been produced by the reaction of soaps with strong alkali bases in molten soaps, alcohol, and ethylene glycol monomethyl ether (U.S. Pat. No. 2,389,260, U.S. Pat. No. 2,242,230 & U.S. Pat. No. 2,343,644). These reactions are inefficient as they require the multiple steps of formation of the fatty acid followed by production of soap from the fatty acids, and subsequently increasing the temperature to isomerize the linoleic soap. The CLA product is generated by acidification with a strong acid (sulfuric or hydrochloric acid) and repeatedly washing the product with brine or $CaCl_2$.

CLA has been synthesized from fatty acids using $SO_2$ in the presence of a substoichiometric amount of soap forming base (U.S. Pat. No. 4,381,264). The reaction with this catalyst produced predominantly the all trans configuration of CLA.

Efficient synthesis of cis,trans-9,11-octadecadienoic from ricinoleic acid has been achieved (U.S. Pat. No. 5,892,074). This synthesis, although efficient, uses expensive elimination reagents such as 1,8-diazobicyclo-(5,4,0)-undecene. For most applications the cost of the elimination reagent increases the production cost beyond the level at which commercial production of CLA is economically viable.

Water may be used in place of alcohols in the production of CLA by alkali isomerization of soaps (U.S. Pat. No. 2,350,583, U.S. Pat. No. 4,164,505). When water is used for this reaction it is necessary to perform the reaction in a pressure vessel whether in a batch (U.S. Pat. No. 2,350,583) or continuous mode of operation (U.S. Pat. No. 4,164,505). The process for synthesis of CLA from soaps dissolved in water still requires a complex series of reaction steps. Bradley and Richardson (*Industrial and Engineering Chemistry* February 1942 vol 34 no2 237–242) were able to produce CLA directly from soybean triglycerides by mixing sodium hydroxide, water and oil in a pressure vessel. Their method eliminated the need to synthesize fatty acids and then form soaps prior to the isomerization reaction. However, they reported that they were only able to produce an oil with up to 40% CLA. Quantitative conversion of the linoleic acid in soybean oil to CLA would have produced a fatty acid mixture with approximately 54% CLA.

Commercial conjugated linoleic acid often contains a mixture of positional isomers that may include trans,cis-8,10-octadecadienoic acid, cis,trans-9,11-octadecadienoic acid, trans,cis-10,12-octadecadienoic acid, and cis,trans-11,13-octadecadienoic acid (Christie, W. W., G. Dobson, and F. D. Gunstone, (1997) Isomers in commercial samples of conjugated linoleic acid. J. Am. Oil Chem. Soc. 74,11,1231).

OBJECT OF INVENTION

One object of this invention is to provide a method of production of CLA using soapstock and other by-products from the refining of vegetable oils that are rich in linoleic acid.

BRIEF STATEMENT OF INVENTION

By one aspect of this invention there is provided a process for producing a salt of conjugated linoleic acid comprising; refining a linoleic acid rich vegetable oil with a solution selected from the group consisting of water, glycerol and glycol solutions containing an alkali so as to produce a soapstock containing salts of linoleic acid; reacting said soapstock with a substoichiometric addition of an alkali at a temperature of at least 170° C.; and liberating said salt of conjugated linoleic acid by addition of at least one of the group consisting of an acid, a monovalent salt solution and a polyvalent salt solution.

DETAILED DESCRIPTION OF PREFERRED EMBODIMENTS

The process of the present invention quantitatively converts soapstocks derived from linoleic acid rich oils to salts of conjugated linoleic acid using a substoichiometric amount of alkali. The process involves blending soapstock derived from vegetable oil rich in linoleic acid, with less than one mole of alkali per mole of acyl groups. The soapstock may also include fatty acids, partial glycerides, waxes and lecithin gums which may increase the amount of alkali required to sustain the reaction. The vegetable oil used in refining may include flaxseed, cottonseed, cucumber, grape seed, corn, safflower, soybean, sunflower or walnut oil or any other oil, wax or ester that is rich in linoleic acid. The reaction will proceed if sodium metal, sodium hydroxide, sodium alkoxylate, potassium metal, potassium hydroxide or potassium alkoxylate or solutions thereof are used as the added alkali. A portion of the alkali included in the reaction may be supplied in the form of calcium hydroxide or calcium oxide. The reaction proceeds at temperatures above 170° C. and the reaction accelerates with increases in temperature. In preferred embodiments, the reaction is conducted above 180° C. As the reaction mixture may contain water it may be necessary to confine the reaction in a sealed pressure vessel.

The reaction proceeds very rapidly at temperatures above 200° C. and the reaction is sensitive to small changes in temperature. The reaction must be maintained at a homogeneous temperature or the reaction will not proceed uniformly. Homogeneous temperature is achieved by vigorous stirring or turbulent flow conditions. In a preferred embodiment the reaction mixture is prepared with a substoichiometric level of KOH and heated to the reaction temperature of 210° C. for 4 hours.

After the reaction is complete the mixture is cooled for separation of the reaction products and by-products. In a preferred embodiment, acid is added to the reaction mixture to hydrolyse the soaps and the reaction mixture is then cooled to between 120° C. and 80° C. It is preferred to bring the pH of the contents of the reactor to pH 4 or less through the addition of either a mineral or organic acid. Acids that may be used include, but are not limited to, hydrochloric acid, sulfuric acid, phosphoric acid and citric acid. It is found that the use of sulfuric and hydrochloric acid is problematic in that these strong acids may react chemically with the CLA during separation. The preferred embodiment of this invention involves the use of phosphoric acid or citric acid to hydrolyse the soaps. When phosphoric acid is used the waste solution can be neutralized and used as a surface applied fertilizer and there are no disposal costs for discarding this product. The hydrolysed soaps form an intractable emulsion in the reactor at 100° C. The emulsion can readily be broken by the addition of one of several demulsifiers which are acceptable for use in food and cosmetic systems.

Reaction progress was determined by gas liquid chromatography of the free fatty acids using a J&W DB-FFAP column (30 M by 0.32 micrometer ID, coating thickness 0.25 micrometer).

EXAMPLES

Example 1
Refining of Safflower Oil with Aqueous Potassium Hydroxide in Water Twenty liters of crude cold pressed safflower oil with a free fatty acid level of 0.2% was placed in a 25 L stainless steel pot and heated to 80° C. One hundred mL of 20% w/w of warm (80° C.) aqueous potassium hydroxide was added to the steel pot and the contents were stirred vigorously for 4 minutes after which they were allowed to settle for 4 hours. After 4 hours the upper layer was decanted from the container and the decanted material was found to contain 0% free fatty acids and 17 PPM soaps. The upper layer was further refined with silica to reduce the soaps to undetectable levels. The lower layer was placed in a 2 L separating funnel and allowed to separate until the upper layer became clear (1 h). The lower layer was recovered and placed into 200 mL centrifuge bottles and centrifuged in a swing-out rotor at 2,000×g for 5 min. The upper layer was decanted and the contents of the lower soap layer were combined and the content of soap and residual glycerides was determined.

Example 2
Refining of Safflower Oil with Solid Potassium Hydroxide in Glycerol Conditions were similar to those described in example 1 except that the solution of aqueous alkali was replaced with a solution of alkali in glycerol.

Example 3
Conversion of Aqueous Soapstock to CLA

Seventy five grams of soapstock prepared as described in example 1 was placed in a 1 L stirred pressure reactor with 325 mL of water to which 10 g of potassium hydroxide pellets were added. The reactor was sealed and the mixture stirred and heated to 230° C. for 4 hours. Samples were taken from the reactor at 1 hour intervals. After the reaction was complete the reactor was cooled to 100° C. After 4 hours most of the linoleic acid had been converted to conjugated linoleic acid isomers.

Example 4
Conversion of Glycerol Soapstock to CLA

One hundred grams of soapstock prepared as described in example 2 were placed in a 1 L glass beaker and 8 grams of KOH dissolved in 8 g of glycerol was added to the soap. The beaker was placed on a temperature controlled stirring hot plate and a Teflon™ coated stirring rod was placed in the beaker. The contents of the beaker were heated to 200° C. for 3 hours. Samples were taken every hour to follow the course of the reaction. After 3 hours the contents of the beaker were allowed to cool to 100° C. After 3 hours most of the linoleic acid had been converted to conjugated linoleic acid isomers.

Example 5
Extraction of CLA Salts Using Brine

The sodium soap of linoleic acid was produced by reacting 500 g of the soapstock prepared as described in example 1. In this example, after the reaction mixture had cooled to 100° C., 500 g of the reaction mixture was removed and added to 800 mL of a saturated sodium chloride solution. The diluted reaction mixture was centrifuged at 2,000×g for 5 minutes to separate the products into two layers. The upper layer of soaps was recovered and washed a second and third time with 800 mL of saturated sodium chloride solution. The thrice washed sodium soaps formed a coarse soapy solid which was dried under vacuum to remove residual water.

Example 6
Extraction of CLA Using Calcium Chloride

The potassium soap of linoleic acid was produced by first reacting 500 g of the soapstock prepared as described in example 1. In this example after cooling the reaction mixture to 100° C. the potassium soaps were converted to calcium soaps by adding 98 g of calcium chloride to the 800 g reaction mixture. The addition of calcium salt increased the viscosity of the entire reaction mixture and a coarse granular material appeared to form. The mass was transferred to a Waring blender and 500 grams of deionized water were added to the blender. The contents of the blender were homogenized for 60 seconds on a low setting and the contents of the blender were placed on a Tyler 100 mesh screen. A coarse fraction of calcium soaps was retained on the screen while a fine fraction and the reaction solution passed through the screen. The coarse fraction was washed twice with 400 mL of water to remove residual glycerol. The fine fraction was recovered by centrifugation and decanting the upper layer. The fine fraction was found to be less than one percent of the solids.

Example 7
Synthesis of CLA from Commercial Sunflower Soapstock

Sunflower soapstock was obtained from a local oilseed crushing plant. Four hundred grams of soapstock were mixed with 400 mL of distilled water and 30 grams of sodium hydroxide in a stirred pressure reactor. The reactor was sealed and the contents of the reactor were heated to 210° C. for 3 hours. The temperature of the reactor was then raised to 220° C. and the contents were reacted for an additional 3 hours. Taking samples every hour from the sample port allowed monitoring of CLA production. Samples were prepared for gas chromatography by the addition of 5 g of soapstock to 3 g of ethanol and mixing the solution. The mixed solution was acidified with 2 mL of phosphoric acid. The fatty acid upper layer that separated after treatment was filtered, diluted in hexane and injected on a DB-FFAP column in a gas chromatograph equipped with a flame ionization detector.

What is claimed is:

1. A process for producing a salt or free acid of conjugated linoleic acid comprising: refining a linoleic acid rich vegetable oil with a solution selected from the group consisting of water, glycerol and glycol solutions containing an alkali so as to produce a soapstock containing salts of linoleic acid; reacting said soapstock with a substoichiometric addition of an alkali, at a temperature of at least 170° C., and liberating said salt of conjugated linoleic acid by addition of at least one of the group consisting of an acid, a monovalent salt solution and a polyvalent salt solution.

2. A process, as claimed in claim 1, where the soapstock is derived by refining a vegetable oil selected from the group consisting of flaxseed, cottonseed, cucumber, grapeseed, corn, safflower, soybean, sunflower and walnut oil.

3. A process, as claimed in claim 1, wherein said alkali is selected from the group consisting of sodium metal, sodium hydroxide, sodium alkoxylate, potassium metal, potassium hydroxide and potassium alkoxylate.

4. A process, as claimed in claim 1, wherein mixtures of two said alkalis are used to catalyse the conversion of the linoleate soaps to conjugated linoleate soaps.

5. A process, as claimed in claim 4, wherein said alkalis are selected from the group consisting of potassium hydroxide, sodium hydroxide, potassium carbonate, sodium carbonate, calcium hydroxide and calcium oxide.

6. A process, as claimed in claim 1, where said acid is selected from the group consisting of hydrochloric, sulfuric, phosphoric and citric acid.

7. A process, as claimed in claim 6, including the step of separating into two phases by addition of a tannin or condensed tannin.

8. A process, as claimed in claim 6, including the step of separating into two phases by addition of a polyethylene glycol with a molecular weight greater than 106 Daltons.

9. A process, according to claim 6, including the step of separating into two phases by the addition of a monohydric alcohol.

10. A process, as claimed in claim 9, wherein said monohydric alcohol is selected from the group consisting of methanol, ethanol, butanol, isopropanol, and n-propanol.

11. A process, as claimed in claim 1, wherein said monovalent salt is a cationic salt of sodium, potassium, lithium or caesium.

12. A process, according to claim 1, where said polyvalent salt is a cationic salt of calcium, magnesium, zinc, copper, aluminum, iron, or chromium.

* * * * *